US005597560A

United States Patent [19]
Bergamini et al.

[11] Patent Number: 5,597,560
[45] Date of Patent: Jan. 28, 1997

[54] DICLOFENAC AND TOBRAMYCIN FORMULATIONS FOR OPHTHALMIC AND OTIC TOPICAL USE

[75] Inventors: Michael V. W. Bergamini, Alella; José A. Vallet Mas, Barcelona; Gemma T. Cabello, El Masnou; Antonio L. Cabrera, Barcelona, all of Spain

[73] Assignee: Laboratorios Cusi, S.A., Spain

[21] Appl. No.: 419,387

[22] Filed: Apr. 10, 1995

[30] Foreign Application Priority Data

May 17, 1994 [ES] Spain ................................. 9401078

[51] Int. Cl.$^6$ ................................................ A61K 31/74
[52] U.S. Cl. ............................ 424/78.04; 424/78.05; 514/912; 514/914
[58] Field of Search ........................ 424/78.04, 78.05; 514/912, 914

[56] References Cited

U.S. PATENT DOCUMENTS

| | | | |
|---|---|---|---|
| 4,087,538 | 5/1978 | Portnoff | 514/420 |
| 4,407,792 | 10/1983 | Schoenwald et al. | 514/397 |
| 4,478,822 | 10/1984 | Hasam et al. | 424/94.6 |
| 4,668,506 | 5/1987 | Bawa | 424/429 |
| 4,829,088 | 5/1989 | Doulakas | 514/567 |

FOREIGN PATENT DOCUMENTS

| | | |
|---|---|---|
| 2013188 | 9/1990 | Canada . |
| 0038698A2 | 10/1981 | European Pat. Off. . |
| 0306984A1 | 3/1989 | European Pat. Off. . |
| WO89/09057 | 10/1989 | WIPO . |

OTHER PUBLICATIONS

*Human Conjunctivitis,* Howard M. Leibowitz, MD, et al., Arch Ophthalmol, vol. 94, Oct. 1976, pp. 1752–1756.

*Association diclofenac–dexamethasone dans le traitement de l'inflammation postopératoire: étude prospective en double–insu,* Dr. Philippe Othenin–Girard, et al., Klin. Mbl. Augenheilk, 200, 1992, pp. 362–366.

*The Effect of 0.1% Indomethacin Eyedrops on Cataract Surgery,* Journal of Ocular Pharmacology, vol. 7, No. 1, 1991, pp. 77–81.

*The Effect of Ketorolac Tromethamine in Reducing Postoperative Inflamation: Double–Mask Parallel Comparison with Dexamethasone,* Allan J. Flach, MD, et al., Ann Ophthalmol 1989; 21:407–411.

*Infections of the Eye—35. Endophthalmitis,* David W. Parke II, et al., pp. 563–583.

*Incompatibility of indometacin and benzalkonium in eye drops due to ion–pair formation,* S. M. Dreijer–Van Der Glas, et al., vol. 9, 1987, Pharmaceutisch Weekblad Scientific Edition, pp. 29–32.

*Effects of Pretreatment with Mydriatics on Intraocular Penetration of 0.1% Pranoprofen,* Takahiro Ogawa, et al., Jpn J Ophthalmol, vol. 37: 47–55, 1993.

*Prediction of Skin Permeability of Drugs: Comparison of Human and Hairless Rat Skin,* Yasunori Morimoto, et al., J. Pharm. Pharmacol. 1992, 44: 634–639.

*Binary Diclogenac Diethylamine–Water Systems: Micelles, Vesicles and Lyotropic Liquid Crystals,* Katrin Kriwet, et al., Eur. J. Pharm. Biopharm, 39 (6) 234–238, 1993.

*Degradation of Tobramycin in Aqueous Solution,* Michael Brandl and Leo Gu, Drug Development and Industrial Pharmacy, 18(13), 1423–1436, 1992.

(List continued on next page.)

*Primary Examiner*—Carlos Azpuru
*Attorney, Agent, or Firm*—Wigman, Cohen, Leitner & Myers, P.C.

[57] ABSTRACT

This invention includes a pharmaceutically acceptable formulation of Diclofenac, Tobramycin, a solubility agent and, optionally, excipients, tonicifiers, buffers, viscosity modifying agents, preservatives, and chelating agents, at a pH from greater than 7.0 to about 9. The invention also discloses the use of this pharmaceutically acceptable formulation of an antibiotic and NSAIDs to treat eye and ear conditions accompanied by infection and inflammation.

96 Claims, 4 Drawing Sheets

OTHER PUBLICATIONS

*Spectrophotometric Method for Determination of Tobramycin, Apramycin and Kanamycin in Formulations,* P. R. Bontchev, et al., Mikrochimica Acta (wien) 1984 III, 459–465.

*The Top Ten NSAIDs – A molecular modelling study,* S. Winiwarter, et al., Pharmaceutica Acta Helvetiae 68 (1994) 181–189.

*Conjunctival Disorders,* Current Veterinary Therapy X Small Animal Practice, Cecil P. Moore, D.V.M., 1989, pp. 673–678.

*A New Corticosteroid–Antibiotic Preparation in Eye and Ear Infections,* General Practitioner Clinical Trials, Alexander, J. et al., Jul., 1966, vol. 197: 94–96.

*Canine Conjunctiva and Nictitating Membrane,* Veterinary Ophthalmology, Dennis E. Brooke, pp. 290–304, 1991.

*Diseases of the Ear,* Textbook of Veterinary Internal Medicine — Diseases of the Dog and Cat, vol. I, Dennis W. Macy, pp. 246–257.

American Academy of Ophthalmology, Final Program, Scientific Posters, p. 101.

XXVIIth International Congress of Ophthalmology '94, Final Program, Scientific Papers.

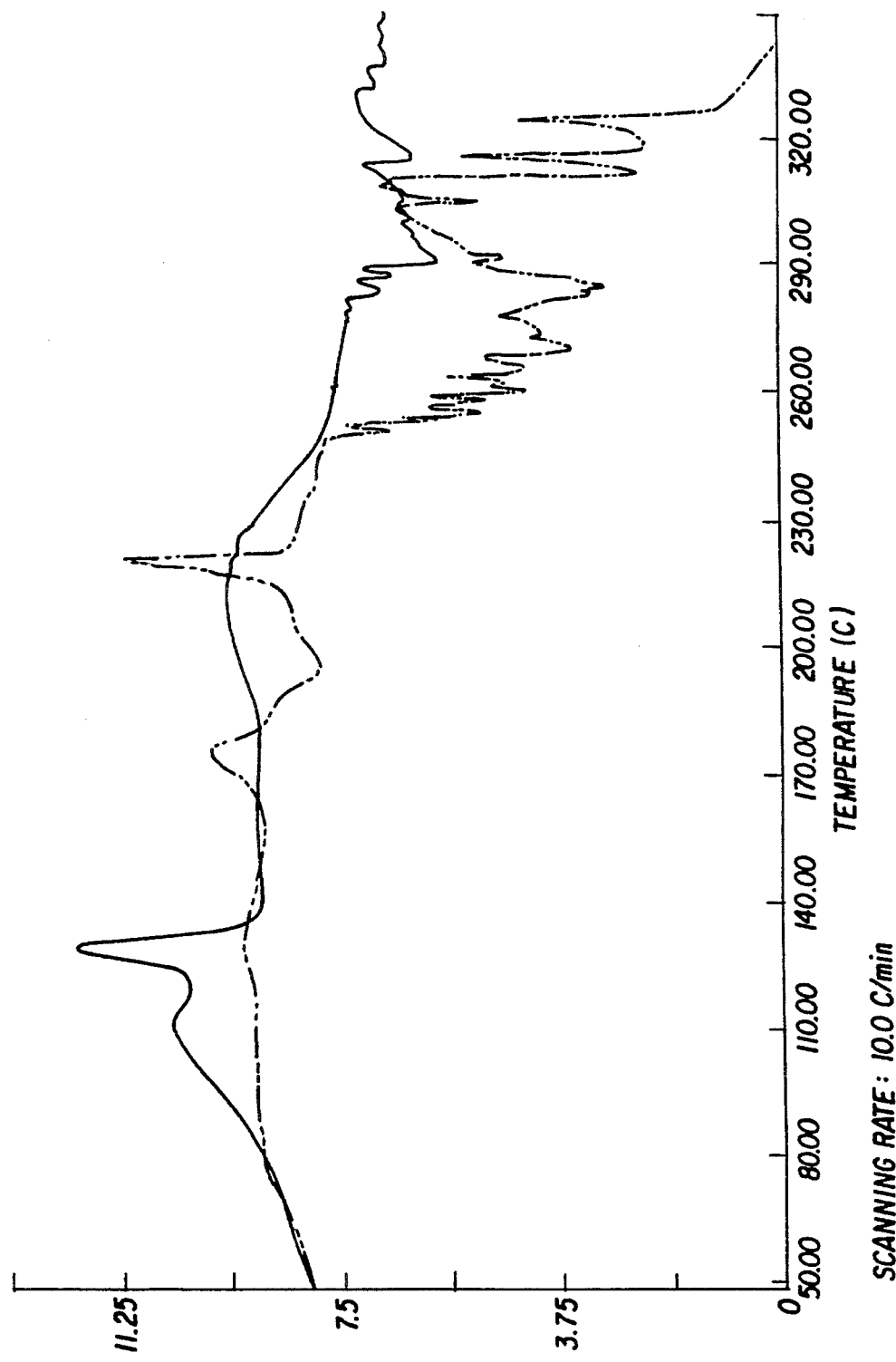

DICLOFENAC AND TOBRAMYCIN FORMULATIONS FOR OPHTHALMIC AND OTIC TOPICAL USE

FIELD OF THE INVENTION

The present invention relates to medical formulations used in the treatment of eye and ear conditions which may be accompanied by infection and inflammation.

BACKGROUND OF THE INVENTION

In ophthalmology, the use of a combination of an antibiotic and an anti-inflammatory drug for the treatment of inflammation associated with infection of the anterior ocular segment, especially conjunctivitis, has been found useful. For example, Leibowitz HM et al. Human Conjunctivitis. Arch Ophthalmol, 1976; 94:1752–6 report that the combination of a corticosteroid and an antibiotic is more effective than the antibiotic alone in the treatment of bacterial acute conjunctivitis.

Non-steroid anti-inflammatory drugs (NSAIDs) were introduced to ophthalmology as an alternative to corticosteroids. It is presently thought that the efficacy of available NSAIDs is comparable to that of the weaker corticosteroids. However, NSAIDs lack the adverse side effects associated with corticosteroids such as the increase in intraocular pressure and the unfavorable immune-suppressant effect that corticosteroids have with viral, fungal, tubercular and other types of infections.

In surgical treatment of the anterior segment of the eye, for example, in cataract surgery, post-operative inflammation can be reduced by the pre-operative and post-operative use of NSAIDs administered to the eye.

There is a correlation between the blepharoconjunctival microbial flora present in the pre-operative stage of cataract surgery and the infectious agents isolated from post-operative endooophthalmitis. For this reason, it is common practice to sterilize or disinfect the external eye structure, both prior to surgery and post-operatively, until there is no longer a possibility of infection in the surgical wound, by treatment with an antibiotic. A combination of antibiotics and either asteroid or a NSAID is also used for treatment of ear infections and ear injuries. This was described by Alexander J et al. A new corticosteroid-antibiotic preparation in eye and ear infections. General Practitioner Clinical Trials 1966; 176:94–96 herein incorporated by reference.

The use of a combination of asteroid and an antibiotic for treatment of eye and ear disorders in veterinary medicine is well known. The same drugs used to treat humans are also used to treat animals, since the eye and ear disorders that are common in veterinary practice have the same physiopathology as human disorders. This is described by Moore CP. Conjuntival disorders. In Current Veterinary Therapy, X Small Animal Practice. Philadelphia: WB Saunders Company, 1989, herein incorporated by reference, Brooks DE. Canine conjunctiva and nictating membrane. In Veterinary Ophthalmology. 2nd Ed. Edited by Gelatt KN. Philadelphia: Lea and Febiger, 1991, herein incorporated by reference and Macy DW. Diseases of the ear. In Textbook of Veterinary Internal Medicine. Diseases of the dog and cat. Edited by Ettinger SJ. Philadelphia: Saunders Company, 1989, herein incorporated by reference.

The use of steroidal anti-inflammatory agents with antibiotics in general and with Tobramycin in particular is well known. This has been described by Cagle et al. in their PCT application WO 89/09057, herein incorporated by reference, where Cagle uses the steroids Dexamethasone, Fluorometholone and Fluorometholone acetate with Tobramycin for treatment of eye infections accompanied by inflammation and by Leibowitz HM et al. 1976 as previously mentioned.

The use of a NSAID with an antibiotic, however, is not well documented, and no combination of a NSAID and an antibiotic has been marketed. Canadian Patent Application No. 2,013,188 (Fu et al.), describes an ophthalmic formulation comprising an NSAID with Tobramycin in a solution with a suitable preservative. The preferred ophthalmic formulation of Fu et al. used the NSAID ketorolac tromethamine with the antibiotic Tobramycin. The preferred ophthalmic formulation of Fu et al. comprises ketorolac tromethamine, Tobramycin, a non-ionic surface active agent, preferably Octoxymol 40, and a preservative selected from the group of quaternary ammonium compounds. Fu et al. reports that the use of non-ionic surface active agents, especially polyoxyethylene alkylphenol surfactants, avoids the unacceptable interactions between NSAID and quaternary ammonium compounds, wherein the NSAID and quaternary ammonium compound form a complex that is either insoluble or retards the absorption of the NSAID.

However, as will be described in greater detail hereinafter, when we attempted to prepare a formulation of Tobramycin and Diclofenac, as possibly suggested by Fu et al., we discovered that the formulation of Tobramycin and Diclofenac formed a precipitate which would be pharmaceutically unacceptable in a formulated product.

Hence, up until our invention, there still was a need for a pharmaceutically acceptable formulation of Tobramycin and Diclofenac for ophthalmological and otic use.

SUMMARY OF THE INVENTION

The present invention relates to a composition—and method of using the composition—which comprises a non-steroidal anti-inflammatory drug, Diclofenac, an antibiotic of the aminoglycoside family, Tobramycin, a solubility agent and the preservatives, excipients, buffers and tonicifiers needed for an acceptable medicament. This composition of the present invention is a pharmaceutically acceptable solution; it has an acceptable shelf-life and does not form a pharmaceutically unacceptable precipitate over its shelf life. This composition can be used to treat eye and ear conditions accompanied by infection and inflammation.

The pathological eye conditions that can be treated with the formulation described in the present invention include conjunctivitis, eye trauma caused by an accident or surgery, eye inflammation and eye infections.

The pathological ear infections that can be treated include otitis externia, otitis meatus, ear inflammation, ear infections and ear trauma.

The formulation can also be used in veterinary practice to treat eye and ear inflammation and eye and ear trauma in a similar manner to the treatment of human eye and ear infections and trauma.

DEFINITIONS

The following terms are defined below:

The term "q.s." means adding a quantity sufficient to achieve a stated function, for example, to bring a solution to a desired volume or adjust pH to a desired value.

The term "treatment" or "treating" means any treatment of a disease or condition, including:

(1) prophylaxis-preventing the disease or condition, that is to say, causing the clinical symptoms of disease not to develop or occur;

(2) inhibiting the disease or condition, that is to say, preventing the development of clinical symptoms; and (3) relieving the disease or condition, that is to say, causing the regression of clinical symptoms.

The term "needs of manufacturing specifications" means the variation in concentration range acceptable in good manufacturing process (GMP) in order to foresee the possible variations during the production of different batches of the product.

Unless stated to the contrary, the percentages stated hereinafter are weight percentages, i.e., grams of material per 100 milliliters of solution, or, for hydrogels, grams of material per 100 grams of final product.

The term "Diclofenac" refers to any pharmaceutically acceptable salt, ester, isomer, or derivative of ortho-(2,6-dichlorophenyl) aminophenyl acetic acid and has the structural formula (I).

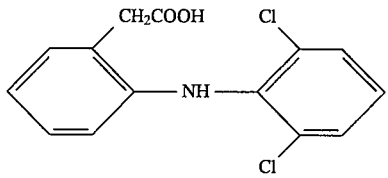

The term "Tobramycin" refers to any pharmaceutically acceptable salt, ester, isomer, or derivative of 4-[2,6-diamino-2,4,6-trideoxy-alpha-D-glycopyranosyl ]-6-]3-amino-3-deoxy-alpha-D-glycopyranosyl]-2-deoxystreptamine and has the structural formula II.

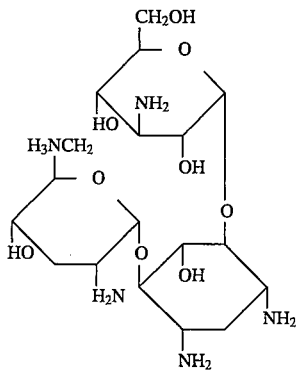

Tobramycin has a broad spectrum of actions against both Gram positive as well as Gram negative organisms, sensitive bacteria include *Staphylococcus aureus, Staphylococcus epidermidis, Streptococcus pneumoniae, Pseudomonas aeruginosa, Escherichia coli, Enterobacter aerogenes, Proteus mirabelis, Klebsiella pneumoniae, Morganella morganii, Haemophilus infiuenzae, Haemophilus aegyptius, Moraxlea lacumata,* and *Acinetobacter calcoaceticus.*

The terms "tromethamine," "tromethanol," "trometamol," are synonyms of the chemical compound trihydroxymethylaminomethane.

The present invention includes isomers, derivatives and pharmaceutically acceptable salts of Diclofenac and Tobramycin.

A formulation in accordance with the invention will have a shelf-life of at least 1 year and preferably 1–2 years. This means that the formulation will remain physically stable, that is to say no precipitate will form over the shelf life of the formulation, that an effective and potent concentration of NSAID and antibiotic will remain at the end of the shelf-life and that the formulation will be able to pass the U.S. Pharmacopeia's antimicrobial challenge at the end of the formulation shelf life. The formulations in accordance with the invention meet these requirements.

DESCRIPTION OF THE INVENTION

A formulation in accordance with the invention comprises a solution of Diclofenac, Tobramycin and a solubility agent to cause Diclofenac and Tobramycin to remain in solution for the shelf life of the product. The formulations used for treatment of either the eye or ear may be identical. Diclofenac or its pharmaceutically acceptable ester, salt, derivative or isomer, has a concentration between about 0.001% and about 0.20%, preferably from about 0.01% to about 0.15%, more preferably from about 0.05% to about 0.10% Diclofenac; Tobramycin has a concentration between about 0.001% to about 1.0%, preferably from about 0.001% to about 0.50%, more preferably from about 0.05% to about 0.40%, and most preferably from about 0.10% to about 0.35%.

The formulations according to the present invention use as solubility agents or surfactants, polyoxysorbates, fatty-acid glycerol-polyethylene glycol esters or a mixture thereof. These compounds are used at a concentration between about 1.0% to about 8.5%, preferably from about 2.0% to about 7.5%, more preferably from about 3.0% to about 7.0%. Other solubility agents such as Octoxynol 40, Tyloxapol and Pluronics can be used as well. The concentration of solubility agent is determined by the need to keep the Diclofenac and Tobramycin in solution. For example, a solution which contains 0.14% Diclofenac and 0.45% Tobramycin includes 3.0% solubility agent to maintain the active ingredients in solution at a pH of 7.5.

Diclofenac is a well known NSAID with a safety profile that is well known after years of experience with the drug. Diclofenac has good systemic and topical efficacy, good systemic and local tolerance and a good topical profile. Diclofenac also does not lead to an increase in intraocular pressure even when Diclofenac is used extensively.

Tobramycin is a well known antibiotic with a good safety profile that is well known after years of pharmaceutical use in ophthalmology. Tobramycin has a broad spectrum of activity and is active against both Gram positive and Gram negative bacteria. The sensitivity shown towards Tobramycin by most Gram positive and Gram negative bacteria involved in eye and ear infections is currently adequate, and Tobramycin seems to have a better profile and work better than other antibiotics.

Tonicity compounds which can be employed are sodium chloride, sodium sulfate, glycerol, mannitol, and sorbitol, as well as any other commonly used tonicity agent. These components are typically used at a level between 0.4% and 7.5%, with the level being selected so as to achieve a formulation of appropriate tonicity.

The formulation also includes pH buffers, such as citrates, borates, phosphates, tris(hydroxymethyl)-amino-methane, and amino acids, such as glycine, lysine, glutamic acid, arginine, and aspartic acid. These pH buffers are introduced into the product to maintain a stable pH and to improve product tolerance by the user. The pH buffers are typically used at levels between about 0.01% to about 3.0%, preferably from about 0.05% to about 2.5%, more preferably from about 0.10% to about 2.0%.

The formulation typically includes viscosity modifying agents, which improve the residence time of the product where it is applied. Typical examples of viscosity modifying agents would include polyvinyl alcohol, polyvinylpyrrolidone, methylcellulose, hydroxypropylcellulose, hydroxyethylcellulose, carboxymethylcellulose and hydroxypropylmethylcellulose. These compounds are typically used at levels between about 0.01% to about 10.0%, preferably from about 0.05% to about 5% and more preferably from about 0.10% to about 3%. The amount of the viscosity modifying agent should be selected so as to obtain a formulation with the desired residence time.

Chelating agents are used in the formulation to eliminate heavy metals and improve the action of the preservative. Examples of chelating agents would include citric acid, ethylene diaminetetraacetic acid (EDTA), EDTA sodium salts, and ethylene glycol-bis(β-aminoethyl ether) N,N,N', N'-tetraacetic acid (EGTA). These compounds are used at a concentration between about 0.01% to about 3.0%, preferably from about 0.05% to about 2.0%, and most preferably from about 0.10% to about 1.0%.

Preservatives, used to inhibit microbial contamination of the product when it is dispensed in multidose containers, can include: quaternary ammonium derivatives, (benzalkonium chloride, benzylammonium chloride, cetylmethyl ammonium bromide, cetylpyridinium chloride), benzethonium chloride, organomercury compounds (Thimerosal, phenylmercury acetate, phenylmercury nitrate), methyl and propyl p-hydroxy-benzoates and salts thereof, betaphenylethyl alcohol, benzyl alcohol, phenylethyl alcohol and phenoxyethanol. The formulation according to the invention can also include mixtures of the preservatives. These compounds are used at effective concentrations, typically from about 0.005% to about 5.0%, depending on the preservative(s) selected. The mount of the preservative used should be enough so that the solution is physically stable, i.e. a precipitate is not formed, and antibacterially effective, that is the formulation with preservative can pass the U.S. Pharmacopeia antimicrobial challenge by a panel of microbes.

The formulation can, as an option, include excipients normally used to obtain pharmaceutical hydrogels. These excipients would include poly(hydroxymethylmethacrylate), poly(N-vinylpyrrolidone), polyvinyl alcohol and acrylic acid polymers such as Carbopol. These compounds are typically used at levels between 0.01% and 25.0%, preferably 0.05% to 15%, more preferably 0.10% to 7%.

The pH of the formulation is chosen so that the formulation remains as a stable, clear and transparent solution. The pH can vary from more than 7.0 to about 9, preferably from about 7.5 to about 9, and most preferably 8.4. To adjust the pH of the formulation to the desired value, the use of acids such as hydrochloric acid or sulfuric acid or bases such as sodium or potassium hydroxide can be used with the pH buffers.

Otic formulations are similar to ophthalmic formulations and the formulations can be used interchangeably. If one were to specifically formulate an otic formulation, one would use more excipient to form a more viscous solution. Hydrogel forming excipients, as was previously described, would be the preferred excipients.

The formulations represented by the invention are physically stable, remain clear and transparent for a useful shelf-life of one to two years and remain antimicrobially effective for the useful shelf life of the product.

For a more detailed discussion of ophthalmic formulations, their preparation and administration, see Remington's Pharmaceutical Sciences, 17th Ed., 1985; 1553–1566, herein incorporated by reference. The otic formulations can be substantially the same as the ophthalmic formulations.

The present invention will become more readily apparent from the comparative examples and working examples which follow.

BRIEF DESCRIPTION OF THE DRAWINGS

FIG. 1(*a*). infra-red spectra of sodium Diclofenac; FIG. 1(*b*). infra-red spectra of Tobramycin; FIG. 1(*c*). infra-red spectra of the precipitate from the formulation of 0.1% sodium Diclofenac, 0.3% Tobramycin, 0.01% BAC, 1.0% Octoxymol 40, pH 8.0. The bands in FIG. 1(*c*) at approximately 1500 cm$^{-1}$ are characteristic of the carboxyl group of sodium Diclofenac and one band at approximately 1050 cm$^{-1}$ is characteristic of the C–N and C–O group of Tobramycin is present.

FIG. 2. Differential Scanning Calorimetry profile from the physical mixture (M) of sodium Diclofenac and Tobramycin and from the precipitate (P) of the formulation of sodium Diclofenac and Tobramycin described in FIG. 1(*c*).

DETAILED DESCRIPTION OF PREFERRED EMBODIMENTS

COMPARATIVE EXAMPLE A

Under the conditions described by Fu et al, a formulation comprising 0.3% Tobramycin, 0.5% Ketorolac tromethamine, 0.01% benzalkonium chloride (BAC) and 0.01% Octoxynol 40 (70% aqueous solution) at pH 7.4 was prepared and yielded a clear, transparent and ophthalmologically useful solution. However, when 0.3% Tobramycin, 0.5% sodium Diclofenac, 0.01% benzalkonium chloride (BAC) and 0.01% Octoxynol 40 (70% aqueous solution) was formulated under the conditions described by Fu et al., that formulation yielded a cloudy solution with suspended particles that was not pharmaceutically acceptable.

COMPARATIVE EXAMPLE B

Figure 1A:
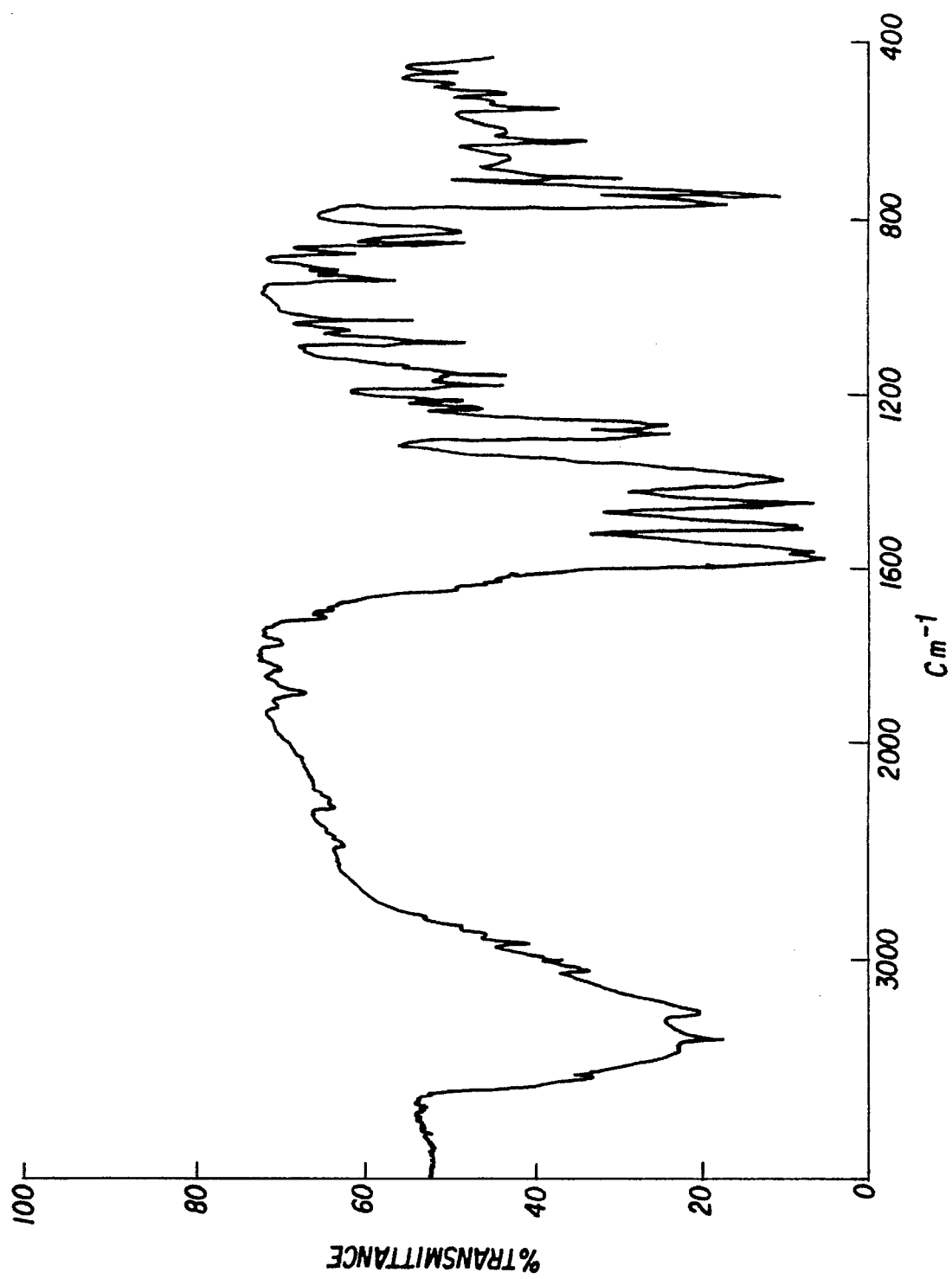
FIG. 1(*a*)–(*c*).
Figure 1B:
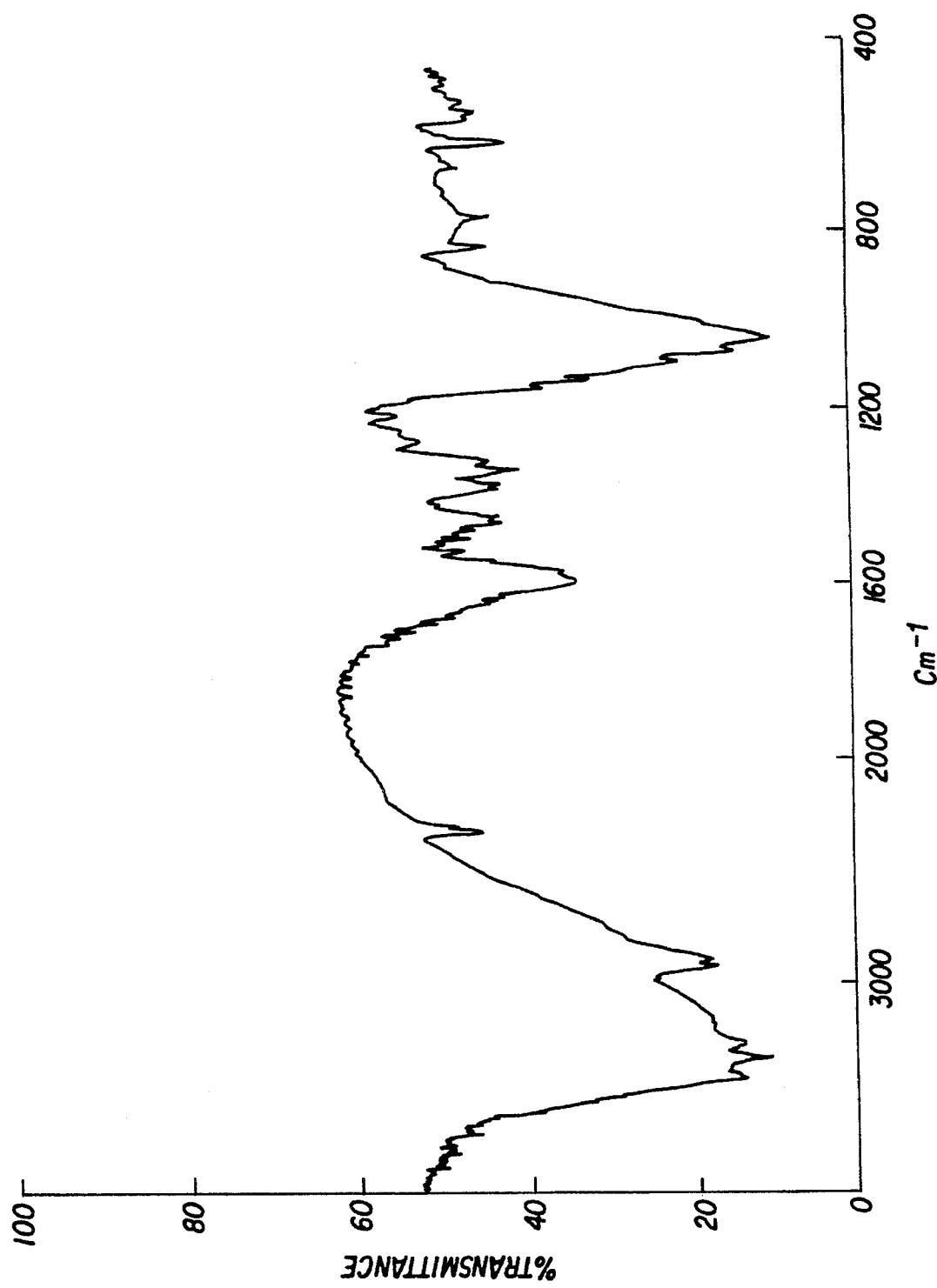
Figure 1C:
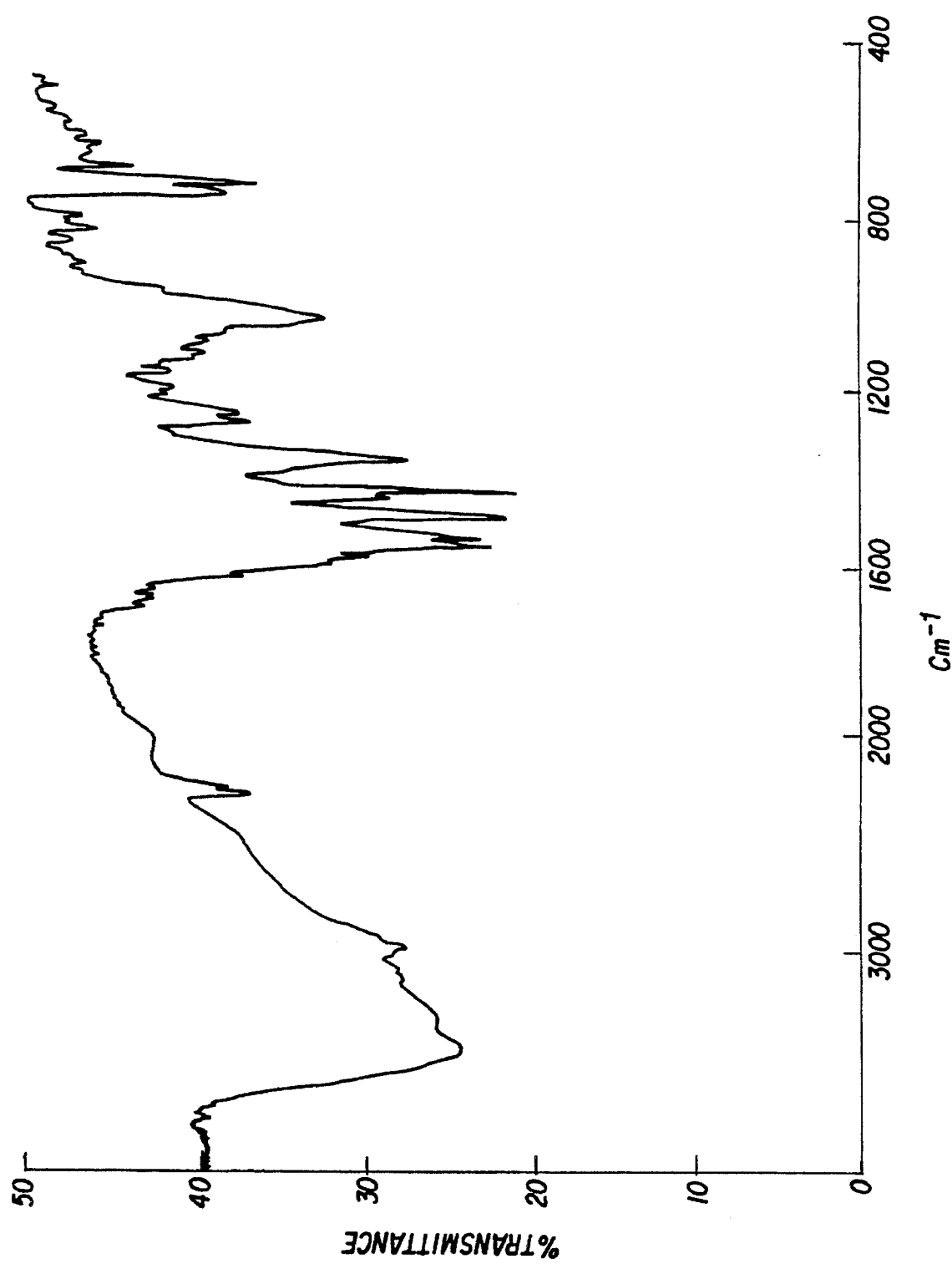

The experiment of Example A was repeated using 0.3% Tobramycin, 0.1% sodium Diclofenac (the concentration normally used in ophthalmology), 0.01% benzalkonium chloride (BAC) and 0.01% Octoxynol 40 (70% aqueous solution) at pH 7.4. This formulation again yielded a cloudy solution with suspended particles that was not pharmaceutically acceptable. The presence of suspended particles is due to the formation of an insoluble complex between Diclofenac and Tobramycin, which was identified by thin-layer chromatography (TLC), HPLC, infra-red spectroscopy (FIG. 1) and DSC (FIG. 2), as will be discussed in greater detail in the following comparative example.

COMPARATIVE EXAMPLE C

A formulation was prepared using 0.1% sodium Diclofenac, 0.3% Tobramycin, 0.01% benzalkonium chloride, 1.0% Octoxynol 40 (70% aqueous solution) and the pH was adjusted to 8.0. As comparative controls, two more formulations were prepared, one with sodium Diclofenac as the active ingredient and the other formulation with Tobramycin as the active ingredient. Samples of the three formulations were stored at 4° C. and 22° C. with the formation of precipitate being followed. The storage temperature of 4° C. was intended to represent a critical storage condition from the point of view of the appearance of a precipitate, but realistic from the point of view of the environmental conditions which a preparation may encounter during its shelf life as a pharmaceutical product. After 41 days at 4° C., the formulation of Diclofenac and Tobramycin developed a precipitate, while the formulations of Diclofenac alone or Tobramycin alone did not develop a precipitate. None of the formulations at 22° C. developed a precipitate after 7.5 months.

The precipitate formed was separated and then analyzed by thin layer chromatography (TLC), HPLC and Infra-Red (IR) spectroscopy. The analysis detected the presence of Diclofenac and Tobramycin. The IR spectrum (FIG. 1) of the precipitate shows the characteristic bands of sodium Diclofenac and Tobramycin that are not found in the spectrum of the separate compounds. The analysis by differential scanning calorimetry (DSC) (FIG. 2) of the precipitate shows a profile clearly different from the profile obtained from the individual compounds as well as the profile obtained from the simple physical mixing of sodium Diclofenac and Tobramycin.

The results obtained show different solubility behavior between Ketorolac and Diclofenac, showing the existence of an interaction between sodium Diclofenac and Tobramycin. The special characteristics of Diclofenac have been disclosed by Kriwet K and Muller-Goyman C. Binary Diclofenac Diethylamine Water systems: micelies, vesicles and lyotropic liquid crystals. Eur J Pharm Biopharm 1993; 39(6):234–238; and Winiwarter S and Roth HJ. The top ten NSAIDs. Pharmaceutica Acta Helvetica 1994; 68:181–189, both herein incorporated by reference.

However, the appearance of a precipitate within 3 days, at 22° C., was observed with a formulation that contained 0.15% sodium Diclofenac, 0.45% Tobramycin, 1.0% Octoxynol 40 (70% aqueous solution) and 0.01% benzyl ammonium chloride (BAC) at a pH of 8.0. These concentrations, which are within the concentrations claimed by Fu et al., were chosen because it is considered that these concentrations are the maximums at which a formulation of Diclofenac and Tobramycin could be found within the normal concentrations used in ophthalmology 0.1% Diclofenac and 0.3% Tobramycin. The concentration of 0.15% Diclofenac and 0.45% Tobramycin would take into account the needs of manufacturing specifications, the potential need for overdosing because of the instability of the Diclofenac and/or the Tobramycin, and the concentration of the formulated product due to evaporative losses from the containers normally used to store these products.

For the purpose of determining the conditions under which a precipitate occurs, the concentration of sodium Diclofenac, the concentration of Octoxymol 40 (70% aqueous solution) and the pH of the final solution was varied while the concentration of benzalkonium chloride (BAC) (0.01%) and Tobramycin (0.3%) was held constant. The concentration of sodium Diclofenac was varied between 0.05 and 0.5%, the concentration of Octoxynol 40 (70% aqueous solution) was varied from 0.01% to 1.0%. The pH values of 6, 7 and 8 were studied. The rest of the components needed for an acceptable ophthalmological medicament were used at the concentrations described in Fu et al., herein incorporated by reference. The initial experimental approach corresponded to a factorial design $3^3$, and, as results were observed, new formulations were developed for the purpose of exploring the conditions that yielded clear and transparent solutions of sodium Diclofenac and Tobramycin. Based on these experiments, the use of high concentrations of surface active agent and alkaline conditions were found to provide the best conditions for obtaining clear and transparent solutions.

We discovered that after 7 months of storage in a refrigerator, clear and transparent solutions were obtained only from the following formulations:

| % sodium Diclofenac | pH | % Octoxynol 40 (70% aqueous solution) |
| --- | --- | --- |
| 0.05 | 6 | 1.0 |
| 0.05 | 7 | 1.0 |
| 0.05 | 8 | 0.5 |
| 0.05 | 8 | 1.0 |

We also discovered that after 7 months storage at 22° C., clear and transparent solutions were obtained only from the following experimental conditions:

| % sodium Diclofenac | pH | % Octoxynol 40 (70% aqueous solution) |
| --- | --- | --- |
| 0.05 | 6 | 1.0 |
| 0.05 | 7 | 1.0 |
| 0.05 | 7 | 0.5 |
| 0.05 | 8 | 0.25 |
| 0.05 | 8 | 0.5 |
| 0.05 | 8 | 1.0 |
| 0.10 | 8 | 1.0 |

The other formulations studied did not provide clear and transparent solutions because a precipitate was obtained either on mixing or during storage. The following formulations yielded a precipitate either on mixing or during storage:

| % sodium Diclofenac | pH | % Octoxynol 40 (70% aq. soln.) |
| --- | --- | --- |
| 0.5 | 8 | 1.0 |
| 0.5 | 7 | 1.0 |
| 0.5 | 6 | 1.0 |
| 0.05 | 8 | 0.01 |
| 0.05 | 7 | 0.01 |
| 0.05 | 6 | 0.01 |
| 0.5 | 8 | 0.01 |
| 0.5 | 7 | 0.01 |
| 0.5 | 6 | 0.01 |
| 0.25 | 8 | 0.01 |
| 0.25 | 8 | 0.5 |
| 0.25 | 8 | 1.0 |
| 0.5 | 8 | 0.5 |
| 0.05 | 6 | 0.5 |
| 0.1 | 8 | 0.5 |
| 0.1 | 7 | 1.0 |
| 0.1 | 6 | 1.0 |
| 0.05 | 7 | 0.25 |
| 0.05 | 6 | 0.25 |

It is noteworthy that Fu et al. prefer a pH of 7.4±0.4 for their formulations, and that even with the greatest concentration of surface active agent described (1.0% Octoxynol 40), a pharmaceutically acceptable, clear and transparent solution cannot be obtained with a concentration of 0.1% sodium Diclofenac and 0.3% Tobramycin at a pH of 7.

As a result of these experiments, we discovered the preferred conditions (pH between 8 and 9; high concentration of solubility agent) necessary to obtain a pharmaceutically acceptable solution of Diclofenac and Tobramycin, thus overcoming the precipitation problems of the Fu et al formulations. The discovered conditions also permit including in the formulation quaternary ammonium compounds as preservatives, since these same conditions also inhibit the unacceptable interaction between Diclofenac and the quaternary ammonium compounds.

It is well known that combinations of antibiotics and antiinflammatory agents intended for topical application are often used to treat different external organs of the body; for example, formulations intended for the topical treatment of the eye are also used for topical treatment of the ear, and, therefore, a combination of antibiotics with an NSAID would be analogously used.

The following formulations are given as representative examples of the compositions included in the present invention, and they should not be considered as restrictions of the scope of the present invention.

EXAMPLE 1

| COMPOSITION | AMOUNT PER 100 ml. |
|---|---|
| Sodium Diclofenac | 0.100 g. |
| Tobramycin | 0.300 g. |
| Benzalkonium chloride | 0.010 g. |
| Polysorbate 80 | 3.000 g. |
| Boric acid | 0.900 g. |
| Sodium tetraborate | 0.450 g. |
| EDTA $Na_2$ | 0.100 g. |
| NaCl q.s. | 300 mOsmol/kg |
| HCl and/or NaOH q.s. | pH 8.4 ± 0.4 |
| Purified water q.s. | 100 ml. |

To prepare an ophthalmic solution, 80% of the water of the formulation was put into a suitable container, and the benzalkonium chloride, boric acid, sodium tetraborate, EDTA $Na_2$, NaCl, Polysorbate 80, Tobramycin and sodium Diclofenac were added. The pH was adjusted with HCl and/or NaOH to 8.4±0.4, water was added to 100 ml., and the resulting solution was filtered through a previously sterilized 0.22 micron filtration system. The obtained solution was dispensed into suitable containers which had been previously sterilized.

EXAMPLE 2

| COMPOSITION | AMOUNT PER 100 ml. |
|---|---|
| Sodium Diclofenac | 0.100 g. |
| Tobramycin | 0.300 g. |
| Benzalkonium chloride | 0.010 g. |
| Polysorbate 20 | 3.000 g. |
| Boric acid | 0.900 g. |
| Sodium tetraborate | 0.450 g. |
| EDTA $Na_2$ | 0.100 g. |
| NaCl q.s. | 300 mOsmol/kg |
| HCl and/or NaOH q.s. | pH 8.4 ± 0.4 |
| Purified water q.s. | 100 ml. |

To prepare an ophthalmic solution, 80% of the water of the formulation was put into a suitable container, and benzalkonium chloride, boric acid, sodium tetraborate, EDTA $Na_2$, NaCl, Polysorbate 20, Tobramycin and sodium Diclofenac were added. The pH was adjusted with HCl and/or NaOH to 8.4±0.4, water was added to adjust the volume to 100 ml, and the resulting solution was filtered through a previously sterilized 0.22 micron filtration system. The obtained solution was dispensed into suitable containers which had been previously sterilized.

EXAMPLE 3

| COMPOSITION | AMOUNT PER 100 ml. |
|---|---|
| Sodium Diclofenac | 0.100 g. |
| Tobramycin | 0.300 g. |
| Benzalkonium chloride | 0.010 g. |
| Glycerol-polyethyleneglycol ricinoleate | 3.500 g. |
| Tromethamine | 0.600 g. |
| EDTA $Na_2$ | 0.100 g. |
| NaCl q.s. | 300 mOsmol/kg |
| $H_2SO_4$ and NaOH q.s. | pH 8.4 ± 0.4 |
| Purified water q.s. | 100 ml. |

To prepare an ophthalmic solution, 80% of the water of the formulation was put into a suitable container, and benzalkonium chloride, Tromethamine, EDTA $Na_2$, NaCl, glycerol-polyethyleneglycol ricinoleate, Tobramycin and sodium Diclofenac were added. The pH was adjusted with $H_2SO_4$ and/or NaOH to 8.4±0.4, the volume was adjusted to 100 ml with water, and the resulting solution was filtered through a previously sterilized 0.22 micron filtration system. The obtained solution was dispensed into suitable containers which had been previously sterilized.

EXAMPLE 4

| SUBSTANCE | AMOUNT PER 100 ml. |
|---|---|
| Sodium Diclofenac | 0.100 g. |
| Tobramycin | 0.300 g. |
| Benzalkonium chloride | 0.010 g. |
| Polysorbate 80 | 3.000 g. |
| Hydroxypropylmethylcellulose | 0.300 g. |
| Boric acid | 0.900 g. |
| Sodium tetraborate | 0.450 g. |
| EDTA $NaCl_2$ | 0.100 g. |
| NaCl q.s. | 300 mOsmol/kg |
| HCl and/or NaOH q.s. | pH 8.4 ± 0.4 |
| Purified water q.s. | 100 ml. |

To prepare an ophthalmic solution, 80% of the water of the formulation was put in a suitable container, and benzalkonium chloride, hydroxypropylmethylcellulose, boric acid, sodium tetraborate, EDTA $Na_2$, NaCl, Polysorbate 80, Tobramycin and sodium Diclofenac were added. The pH was adjusted with HCl and/or NaOH to 8.4±0.4, the volume was adjusted to 100 ml with water, and the resulting solution was filtered through a previously sterilized 0.22 micron filtration system. The obtained solution was dispensed in suitable containers which had been previously sterilized.

EXAMPLE 5

| SUBSTANCE | AMOUNT PER 100 ml. |
|---|---|
| Sodium Diclofenac | 0.100 g. |
| Tobramycin | 0.300 g. |
| Benzalkonium chloride | 0.010 g. |
| Polysorbate 20 | 3.000 g. |
| Hydroxyethylcellulose | 0.500 g. |
| Boric acid | 0.900 g. |
| Sodium tetraborate | 0.450 g. |
| EDTA $Na_2$ | 0.100 g. |
| NaCl q.s. | 300 mOsmol/kg |
| HCl and/or NaOH q.s. | pH 8.0 ± 0.4 |
| Purified water q.s. | 100 ml. |

To prepare an ophthalmic solution, 80% of the water of the formulation was put into a suitable container, and benzalkonium chloride, hydroxyethylcellulose, boric acid, sodium tetraborate, EDTA Na$_2$, NaCl, Polysorbate 20, Tobramycin and sodium Diclofenac were added. The pH was adjusted with HCl and/or NaOH to 8.4±0.4, the volume was adjusted to 100 ml with water, and the resulting solution was filtered through a previously sterilized 0.22 micron filtration system. The obtained solution was dispensed into suitable containers which had been previously sterilized.

EXAMPLE 6

| SUBSTANCE | AMOUNT PER 100 ml. |
|---|---|
| Sodium Diclofenac | 0.100 g. |
| Tobramycin | 0.300 g. |
| Benzalkonium chloride | 0.010 g. |
| Polysorbate 80 | 5.000 g. |
| Boric acid | 0.900 g. |
| Sodium tetraborate | 0.450 g. |
| EDTA Na$_2$ | 0.100 g. |
| NaCl q.s. | 300 mOsmol/kg |
| HCl and/or NaOH q.s. | pH 7.5 ± 0.4 |
| Purified water q.s. | 100 ml. |

To prepare an ophthalmic solution, 80% of the water of the formulation was put into a suitable container, and the benzalkonium chloride, boric acid, sodium tetraborate, EDTA Na$_2$, NaCl, Polysorbate 80, Tobramycin and sodium Diclofenac were added. The pH was adjusted to 7.5±0.4 with HCl and/or NaOH, water was added to 100 ml., and the resulting solution was filtered through a previously sterilized 0.22 micron filtration system. The obtained solution was dispensed into suitable containers which had been previously sterilized.

Although certain presently preferred examples and embodiments of the invention have been described herein, it will be apparent to those skilled in the art to which the invention pertains that variations and modifications of the described examples and embodiments may be made without departing from the spirit and scope of the invention. Accordingly, it is intended that the invention be limited only to the extent required by the appended claims and the applicable rules of law.

What is claimed:

1. An ophthalmologically or otically effective solution comprising:
   between about 0.001% to about 0.20% diclofenac,
   between about 0.001% to about 1.0% tobramycin,
   between 0.25% to about 8.5% of a pharmaceutically acceptable solubility agent, said solubility agent being present in an effective amount which prevents the formation of a precipitate, and
   sufficient solvent to form said ophthalmologically or otically effective solution with a pharmaceutically acceptable shelf-life wherein the pH of said solution is compatible with the eye and wherein the amount of tobramycin and diclofenac is sufficient to treat the eye or ear of a patient in need of treatment.

2. The solution of claim 1 wherein a pharmaceutically acceptable preservative is added to the solution.

3. The solution of claim 2 wherein the preservative is selected from the group consisting of quaternary ammonium derivatives, organomercury compounds methyl p-hydroxybenzoates, methyl p-hydroxybenzoate salts, propyl p-hydroxy-benzoates, propyl p-hydroxy-benzoate salts, bethaphenylethyl alcohol, benzyl alcohol, phenylethyl alcohol, phenoxyethanol and mixtures of the aforesaid compounds.

4. The solution of claim 1 wherein a pH buffer is added to the solution.

5. The solution of claim 4 wherein the pH buffer is selected from the group consisting of citrates, borates, phosphates, tris (hydroxymethyl)-amino-methane, glycine, lysine, glutamic acid, arginine and aspartic acid.

6. The solution of claim 2 wherein a pH buffer is added to the solution.

7. The solution of claim 1 further including a chelating agent.

8. The solution of claim 7 wherein the chelating agent is selected from the group consisting of citric acid, ethylenediaminetetraacetic acid, EDTA sodium salt and ethylene glycol-bis(β-aminoethyl ether) N,N,N',N'-tetraacetic acid (EGTA).

9. The solution of claim 6 further including a chelating agent.

10. The solution of claim 1 wherein a tonicity compound is added to the solution.

11. The solution of claim 10 wherein the tonicity compound is selected from the group consisting of sodium chloride, sodium sulfate, glycerol, mannitol and sorbitol.

12. The solution of claim 9 wherein a tonicity compound is added to the solution.

13. The solution of claim 1 further including a viscosity modifying agent.

14. The solution of claim 13 wherein the viscosity modifying agent is selected from the group consisting of polyvinyl alcohol, polyvinyl pyrrolidone, methyl cellulose, hydroxypropyl cellulose, hydroxyethyl cellulose, hydroxymethyl cellulose and hydroxypropyl cellulose.

15. The solution of claim 9 further including a viscosity modifying agent.

16. The solution of claim 1 further including a hydrogel forming excipient.

17. The solution of claim 16 wherein the hydrogel forming excipient is selected from the group consisting of polyvinyl alcohol, partial acetylated polyvinyl alcohol, poly(hydroxymethyl methacrylate), poly(N-vinylpyrrolidone), acrylic acid polymers and Carbopol.

18. The solution of claim 9 further including a hydrogel forming excipient.

19. The solution of claim 1 wherein the pH of the formulation is between 7.0 and about 9.

20. The solution of claim 9 wherein the pH of the formulation is between 7.0 and about 9.

21. The solution of claim 19 wherein the pH of the formulation is between about 7.5 and about 9.

22. The solution of claim 20 wherein the pH of the formulation is between about 8 and about 9.

23. The solution of claim 1 wherein the solubility agent is selected from polyoxysorbates, fatty-acid glycerol-polyethylene glycol esters, Octoxynol 40, Tyloxapol, Pluronics and mixtures thereof.

24. The solution of claim 9 wherein the solubility agent is selected from polyoxysorbates, fatty-acid glycerol-polyethylene glycol esters, Octoxynol 40, Tyloxapol, Pluronics and mixture thereof.

25. A method of treating an eye or an ear by administering a pharmaceutically effective amount of the solution of claim 1 to the eye or the ear of a patient in need thereof.

26. A method of treating an eye or an ear by administering a pharmaceutically effective amount of the solution of claim 2 to the eye or the ear of a patient in need thereof.

27. A method of treating an eye or an ear by administering a pharmaceutically effective amount of the solution of claim 4 to the eye or the ear of a patient in need thereof.

28. A method of treating an eye or an ear by administering a pharmaceutically effective amount of the solution of claim 6 to the eye or the ear of a patient in need thereof.

29. A method of treating an eye or an ear by administering a pharmaceutically effective amount of the solution of claim 7 to the eye or the ear of a patient in need thereof.

30. A method of treating an eye or an ear by administering a pharmaceutically effective amount of the solution of claim 9 to the eye or the ear of a patient in need thereof.

31. A method of treating an eye or an ear by administering a pharmaceutically effective amount of the solution of claim 10 to the eye or the ear of a patient in need thereof.

32. A method of treating an eye or an ear by administering a pharmaceutically effective amount of the solution of claim 12 to the eye or the ear of a patient in need thereof.

33. A method of treating an eye or an ear by administering a pharmaceutically effective amount of the solution of claim 13 to the eye or the ear of a patient in need thereof.

34. A method of treating an eye or an ear by administering a pharmaceutically effective amount of the solution of claim 15 to the eye or the ear of a patient in need thereof.

35. A method of treating an eye or an ear by administering a pharmaceutically effective amount of the solution of claim 16 to the eye or the ear of a patient in need thereof.

36. A method of treating an eye or an ear by administering a pharmaceutically effective amount of the solution of claim 18 to the eye or the ear of a patient in need thereof.

37. A method of treating an eye or an ear by administering a pharmaceutically effective amount of the solution of claim 19 to the eye or the ear of a patient in need thereof.

38. A method of treating an eye or an ear by administering a pharmaceutically effective amount of the solution of claim 21 to the eye or the ear of a patient in need thereof.

39. A method of treating an eye or an ear by administering a pharmaceutically effective amount of the solution of claim 23 to the eye or the ear of a patient in need thereof.

40. A method of treating an eye or an ear by administering a pharmaceutically effective amount of the solution of claim 24 to the eye or the ear of a patient in need thereof.

41. The solution of claim 1 wherein between about 1.0% to about 8.5% of a pharmaceutically acceptable solubility agent is used.

42. The solution of claim 41 wherein about 0.005% to about of an ophthalmologically and otically acceptable preservative is added to the solution.

43. The solution of claim 41 wherein between about 0.01% to about 3.0% of a ophthalmologically acceptable chelating agent is added to the solution.

44. The solution of claim 42 wherein between about 0.01% to about 3.0% of a ophthalmologically acceptable chelating agent is added to the solution.

45. The solution of claim 41 wherein between about 0.01% to about 3.0% of a ophthalmologically and otically acceptable buffer is added to the solution.

46. The solution of claim 44 wherein between about 0.01% to about 3.0% of a ophthalmologically and otically acceptable buffer is added to the solution.

47. The solution of claim 41 wherein a quantity of tonicifier sufficient to form an ophthalmologically acceptable formulation is added to the solution.

48. The solution of claim 46 wherein a quantity of tonicifier sufficient to form an ophthalmologically acceptable formulation is added to the solution.

49. The solution of claim 41 wherein up to about 10% of an ophthalmologically and otically acceptable viscosity modifying agent is added to the solution.

50. The solution of claim 48 wherein up to about 10% of an ophthalmologically and otically acceptable viscosity modifying agent is added to the solution.

51. The solution of claim 41 wherein about 0.01% to about 25.0% ophthalmologically and otically acceptable hydrogel forming excipient is added to the solution.

52. The solution of claim 47 wherein said tonicifier comprises from about 0.4 to about 7.5%.

53. The solution of claim 48 wherein said tonicifier comprises from about 0.4 to about 7.5%.

54. The solution of claim 1 comprising
about 0.05% to about 0.1% diclofenac,
about 0.1% to about 0.45% tobramycin, and
about 3.0% to about 7.0% solubilizing agent.

55. The composition of claim 54 further including a pH buffer, a chelating agent and a tonicity agent, said composition having a pH of 7.0 to about 9.0.

56. A method of treating an eye or an ear by administering the solution of claim 41 to the eye or the ear of a patient in need thereof.

57. A method of treating an eye or an ear by administering the solution of claim 42 to the eye or the ear of a patient in need thereof.

58. A method of treating an eye or an ear by administering the solution of claim 43 to the eye or the ear of a patient in need thereof.

59. A method of treating an eye or an ear by administering the solution of claim 44 to the eye or the ear of a patient in need thereof.

60. A method of treating an eye or an ear by administering the solution of claim 45 to the eye or the ear of a patient in need thereof.

61. A method of treating an eye or an ear by administering the solution of claim 46 to the eye or the ear of a patient in need thereof.

62. A method of treating an eye or an ear by administering the solution of claim 47 to the eye or the ear of a patient in need thereof.

63. A method of treating an eye or an ear by administering the solution of claim 48 to the eye or the ear of a patient in need thereof.

64. A method of treating an eye or an ear by administering the solution of claim 49 to the eye or the ear of a patient in need thereof.

65. A method of treating an eye or an ear by administering the solution of claim 50 to the eye or the ear of a patient in need thereof.

66. A method of treating an eye or an ear by administering the solution of claim 51 to the eye or the ear of a patient in need thereof.

67. A method of treating an eye or an ear by administering the solution of claim 52 to the eye or the ear of a patient in need thereof.

68. A method of treating an eye or an ear by administering the solution of claim 53 to the eye or the ear of a patient in need thereof.

69. A method of treating an eye or an ear by administering the composition of claim 54 to the eye or the ear of a patient in need thereof.

70. A method of treating an eye or an ear by administering the composition of claim 55 to the eye or the ear of a patient in need thereof.

71. The solution of claim 12 further including a viscosity modifying agent.

72. The solution of claim 12 further including a hydrogel forming excipient.

73. The solution of claim 12 wherein the pH of the solution is between 7.0 and about 9.

74. The solution of claim 15 wherein the pH of the solution is between 7.0 and about 9.

75. The solution of claim 18 wherein the pH of the solution is between 7.0 and about 9.

76. The solution of claim 12 wherein the solubility agent is selected from polyoxysorbates, fatty-acid glycerol-polyethylene glycol esters, Octoxynol 40, Tyloxapol, Pluronics and mixtures thereof.

77. The solution of claim 15 wherein the solubility agent is selected from polyoxysorbates, fatty-acid glycerol-polyethylene glycol esters, Octoxynol 40, Tyloxapol, Pluronics and mixtures thereof.

78. The solution of claim 18 wherein the solubility agent is selected from polyoxysorbates, fatty-acid glycerol-polyethylene glycol esters, Octoxynol 40, Tyloxapol, Pluronics and mixtures thereof.

79. A method of treating an eye or an ear by administering a pharmaceutically effective amount of the solution of claim 20 to the eye or the ear of a patient in need thereof.

80. A method of treating an eye or an ear by administering a pharmaceutically effective amount of the solution of claim 22 to the eye or the ear of a patient in need thereof.

81. The solution of claim 46 wherein between about 0.01% to about 25.0% of an ophthalmologically and otically acceptable hydrogel forming excipient is added to the solution.

82. A method of making the ophthalmologically or otically effective solution of tobramycin and diclofenac of claim 1 comprising the steps of:

dissolving pharmaceutically effective amounts of diclofenac and tobramycin with sufficient solubility agent in an ophthalmologically or otically acceptable solvent to form said solution;

adjusting the pH of said solution from about 7.0 to about 9; and sterilizing said solution, wherein the pharmaceutically effective amount of tobramycin and diclofenac is sufficient to treat the eye or ear of a patient in need thereof.

83. The method of claim 82 wherein a pharmaceutically acceptable preservative is added to said solution.

84. The method of claim 83 wherein a pharmaceutically acceptable preservative is selected from the group consisting of quaternary ammonium derivatives, organomercury compounds, methyl p-hydroxybenzoates, methyl p-hydroxybenzoate salts, propyl p-hydroxy-benzoates, propyl p-hydroxybenzoate salts, betaphenylethyl alcohol, benzyl alcohol, phenylethyl alcohol, phenoxyethanol and mixtures of the aforesaid compounds.

85. The method of claim 82 wherein a pH buffer is added to said solution.

86. The method of claim 85 wherein said pH buffer is selected from the group consisting of citrates, borates, phosphates, tris (hydroxymethyl)-amino-methane, glycine, lysine, glutamic acid, arginine and aspartic acid.

87. The method of claim 82 wherein a chelating agent is added to said solution.

88. The method of claim 87 wherein a chelating agent is selected from the group consisting of citric acid, ethylenediaminetetraacetic acid, EDTA sodium salt and ethylene glycol-bis($\beta$-aminoethyl ether) N,N,N',N'-tetraacetic acid (EGTA).

89. The method of claim 82 wherein a tonicity agent is added to said solution.

90. The method of claim 89 wherein said tonicity agent is selected from the group consisting of sodium chloride, sodium sulfate, glycerol, mannitol and sorbitol.

91. The method of claim 82 wherein a viscosity modifying agent is added to said solution.

92. The method of claim 87 wherein said viscosity modifying agent is selected from the group consisting of polyvinyl alcohol, polyvinyl pyrrolidone, methyl cellulose, hydroxypropyl cellulose, hydroxyethyl cellulose, hydroxymethyl cellulose and hydroxypropyl cellulose.

93. The solution of claim 3 wherein the quaternary ammonium derivatives are selected from the group consisting of benzalkonium chloride, benzylammonium chloride, cetylmethyl ammonium bromide, cetylpyridimium chloride, benzethonium chloride and mixtures thereof.

94. The solution of claim 3 wherein organomercury compounds are selected from the group consisting of thimerosal, phenylmercury acetate, phenylmercury nitrate and mixtures thereof.

95. The method of claim 84 wherein the quaternary ammonium derivatives are selected from the group consisting of benzalkonium chloride, benzylammonium chloride, cetylmethyl ammonium bromide, cetylpyridimium chloride, benzethonium chloride and mixtures thereof.

96. The method of claim 84 wherein the organomercury compounds are selected from the group consisting of thimerosal, phenylmercury acetate, phenylmercury nitrate and mixtures thereof.

* * * * *